United States Patent [19]

Chase et al.

[11] Patent Number: 4,772,127
[45] Date of Patent: Sep. 20, 1988

[54] SURFACE INSPECTION APPARATUS

[75] Inventors: Eric T. Chase, Methuen; Sergey V. Broude, Acton; George S. Quackenbos, Newburyport, all of Mass.

[73] Assignee: QC Optics, Inc., Burlington, Mass.

[21] Appl. No.: 682,794

[22] Filed: Dec. 18, 1984

[51] Int. Cl.⁴ .............................................. G01N 21/00
[52] U.S. Cl. ...................................... 356/338; 356/336
[58] Field of Search ....................... 356/336, 338, 342; 350/270

[56] References Cited

U.S. PATENT DOCUMENTS 3,654,846  4/1972  Wernikoff et al. ................... 350/270
4,402,607  9/1983  McVay et al. ....................... 356/338
4,415,265 11/1983  Campillo et al. ................... 356/338

Primary Examiner—R. A. Rosenberger
Assistant Examiner—Crystal Cooper
Attorney, Agent, or Firm—Joseph S. Iandiorio; Douglas E. Denninger

[57] ABSTRACT

In the surface inspection apparatus disclosed herein, an elongate array of electro-optical shutters is interposed between a laser beam which scans across the surface to be inspected and a photodetector system which collects light scattered from the surface along the scan line. The shutters are operated in a shifting pattern in synchronism with the scanning means thereby to block unwanted regular signal components.

8 Claims, 5 Drawing Sheets

SURFACE INSPECTION APPARATUS

BACKGROUND OF THE INVENTION

The present invention relates to surface inspection apparatus and more particularly to such a system in which a laser beam is scanned across the surface to be inspected and the scattered light is analyzed to detect flaws in or particles on the surface.

It has previously been known to inspect various surfaces by scanning a laser beam across the surface and then analyzing the light scattered to determine the presence of defects or particles on this surface. For example, a system for detecting dust particles on the surface of glass reticle plates is disclosed in co-assigned U.S. Letters Pat. No. 4,402,607 issued Sept. 6, 1983 to Lance McVay and Pedro Lilienfeld. In the system disclosed in that patent, the effects of semi-specular reflection and characteristic regular scattering caused by the pattern on the reticle were minimized, though not eliminated, by the use of a scanning beam which approached the surface at an acute angle and by utilizing only the back-scattered components of the light scattered from the surface being inspected.

While the present invention was devised as an improvement to the system shown in the '607 patent, it has broader application and in many ways overcomes limitations which had characterized this and other prior art systems.

Among the several objects of the present invention may be noted the provision of a novel surface inspection apparatus utilizing a scanned light beam; the provision of surface inspection apparatus having improved sensitivity for defects relative to regular pattern noise in the system; the provision of such apparatus which permits a relatively wide range of scanning and detection angles; the provision of such an apparatus which permits detection and distinguishing of defects of various types; the provision of such apparatus which is highly accurate, which is highly reliable, and which is of relatively simple and inexpensive construction. Other objects and features are in part apparent and in part pointed out hereinafter.

SUMMARY OF THE INVENTION

In surface inspection apparatus constructed in accordance with the present invention, a light beam is scanned in line across the surface to be inspected. Light scattered from the surface along the scan line is collected and coupled to a photodetector. An array of electro-optical shutters is provided adjacent the scan line and is optically interposed between the source of the light beam and the photodetector. Control means are provided for operating the shutters in a shifting pattern which shifts in synchronism with the scanning means and thereby blocks unwanted regular signal components.

BRIEF DESCRIPTION OF THE DRAWINGS

Corresponding reference characters indicate corresponding parts throughout the several views of these drawings.

DETAILED DESCRIPTION OF THE PREFERRED EMBODIMENTS

Figure 1:
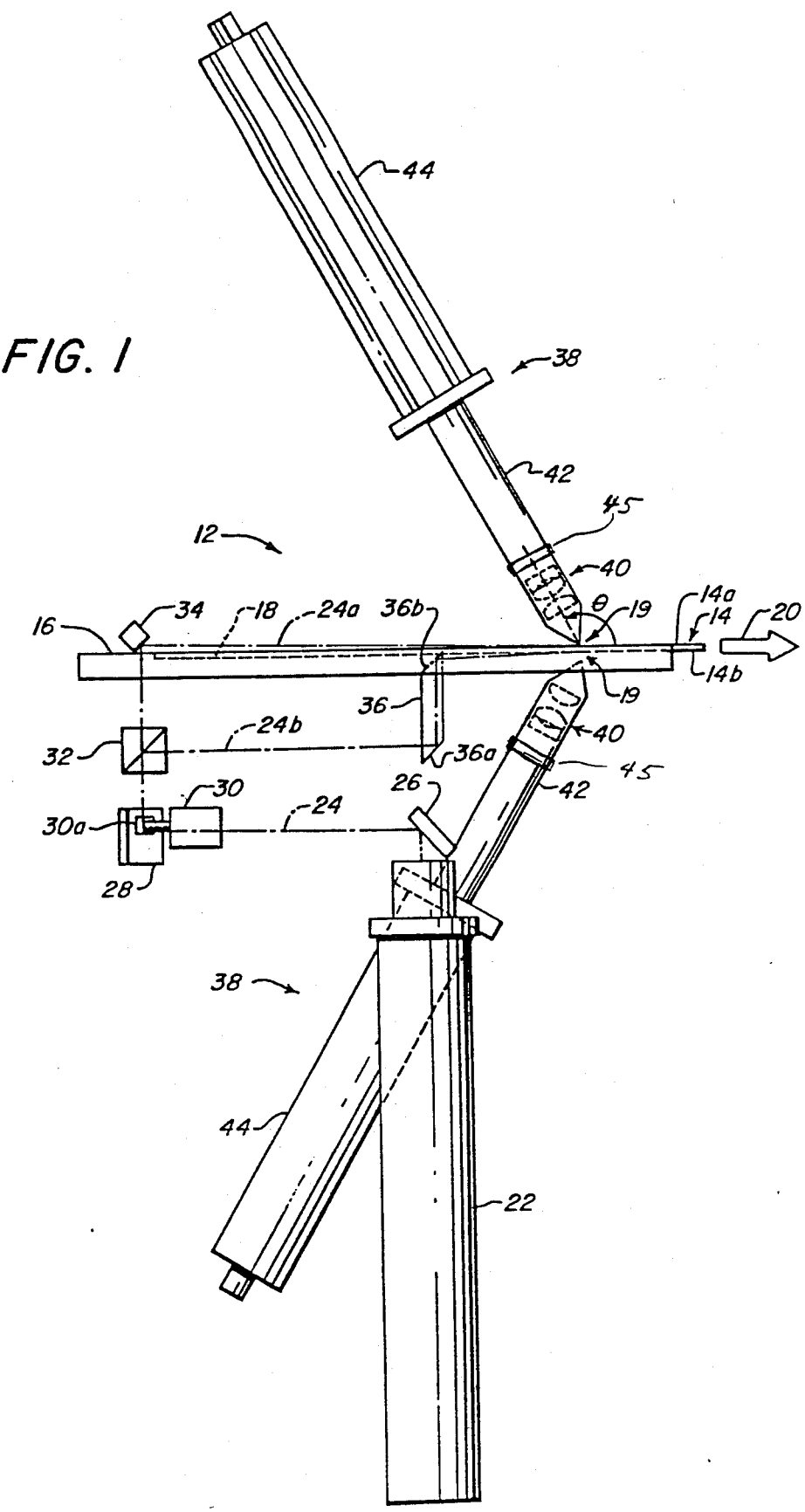
FIG. 1 is a view in side elevation of surface inspection apparatus constructed in accordance with the present invention.
Figure 2:
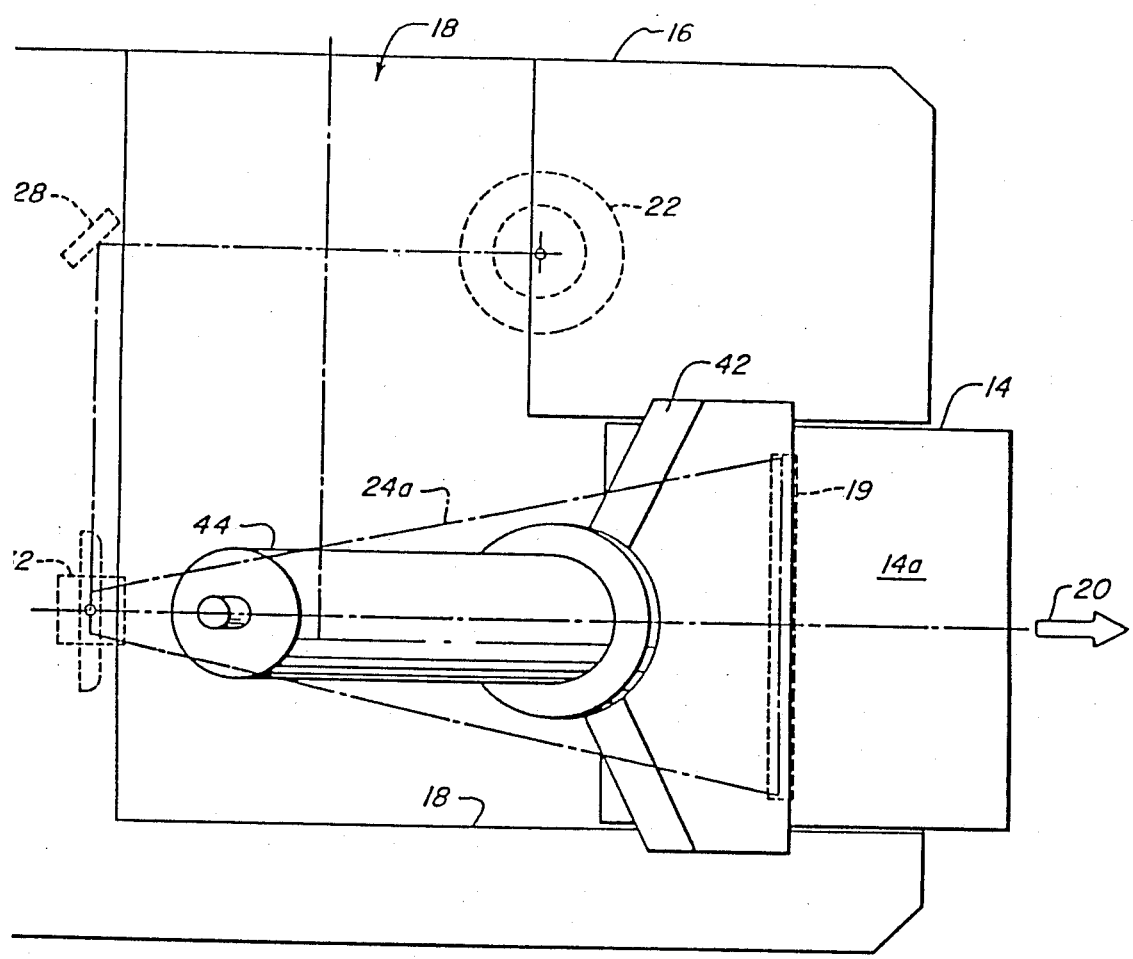
FIG. 2 is a top plan view of the inspection apparatus of FIG. 1.
Figure 3:
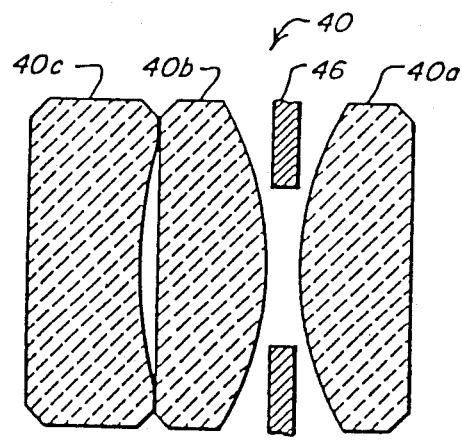
FIG. 3 is a detailed view, in side elevation, of a cylindrical lens triplet employed in the apparatus of FIGS. 1 and 2.

FIGS. 1-3 show, by way of illustration, a system constructed in accordance with the present invention for automatically detecting minute particles such as dust resting on a relatively large-area, flat surface. This representative system is particularly useful in inspecting a glass photographic plate 14, commonly termed a reticle, used in the production of microelectronic circuits. The reticle carries a pattern of dark areas formed by a thin (e.g. 0.6 micrometer) layer of chrome deposited on one of its faces. Typical dimensions for a reticle are 127 mm × 127 mm × 2.29 mm. The projection image area of this reticle, which includes the chrome pattern, is approximately 105 mm square. A notable characteristic of such reticles is that the glass faces themselves as well as the dark chrome pattern will scatter light to some degree.

The detection system 12 includes an air plate 16 with a channel or track 18 formed in its upper surface. The track 18 guides the reticle 14 through the detection system and onto the optical stage of a step-and-repeat projector (not shown) where the reticle is used to expose a wafer. Air nozzles (not shown) mounted in the plate 16 provide both an air bearing and propulsion for the reticle as it moves through the channel 18. The velocity of the reticle advance is substantially constant. An arrow 20 indicates the direction of advance of the reticle from the track 18 onto the optical stage. A significant advantage of the present invention is that the reticle is inspected for the presence of dust particles at a point very near the center of the optical stage, a representative value being six inches.

Each face of the reticle is irradiated over a generally rectangular scanning region by a narrow, high intensity beam 24 of monochromatic radiation. This beam is preferably generated by a laser 22 and can have a wavelength of, for example 630 nm (visible light). The beam is characterized by a small angular divergence, and preferably has a width at the scanning region 19 of approximately 0.5 mm or less measured between the half maxima of the beam intensity profile. The high intensity of the beam is important to provide a good signal to noise ratio when it is scattered from a dust particle located on an upper face 14$a$ or lower face 14$b$ of the reticle 14. A recommended value for the beam intensity is 0.1 W/mm2.

Optical elements which direct the beam 24 from the laser 22 to the reticle scanning region including a first folding mirror 26, a second folding mirror 28, an optical scanner 30 including an oscillating scanning mirror 30a, a beam splitter 32, a third folding mirror 34, and a double reflecting prism 36. The mirror 26 directs the beam from an upward direction as it exits the laser to a horizontal orientation toward the second mirror 28 which in turn reflects the beam horizontally onto the scanning mirror 30a of the optical scanner 30. The scanning mirror 30a is inclined at a 45 degree angle with respect to the horizontal plane of the beam path determined by the mirrors 26 and 28 to direct the beam upwardly to the beam splitter 32. The scanner mirror oscillates in a manner which scans the beam in a fan-like manner as is best seen in FIG. 2. The beam splitter 32 is preferably a conventional cubic splitter that divides the incident beam into an upper scanning beam 24a and a lower scanning beam 24b of substantially equal intensity. The beam 24a proceeds upwardly through an aperture in the plate 16 to the third folding mirror 34 which directs the beam onto the upper face 14a of the reticle. The lower beam 24b, reflected by the beam splitter 32, proceeds along a substantially horizontal path to the prism 36 where it is internally reflected twice at faces 36a and 36b emerging from the prism 36 onto the lower face 14b of the reticle.

The optical scanner 30, which can be the unit sold by General Scanning, Inc. under the trade designation Model No. G115, has a mirror 30a which oscillates at a frequency of approximately 50 Hz. The amplitude of the oscillation is sufficient to scan the beam laterally in a direction generally perpendicular to the direction of advance 20 of the reticle over the projection image area which will be photolithographically reproduced. For a typical 127 mm square reticle, the beam therefore scans laterally over the reticle for a distance of approximately 105 mm. Because of the grazing angle of inspection of the beam, the beam irradiates a face area of the reticle extending longitudinally (in the direction 20) for approximately two inches with the precise length depending on the inspection angle and the beam width. This irradiated area is the scanning region of the faces 14a and 14b.

The beam splitter 32 is spaced from the lower face of the plate 16 so that the lower split beam 24b reflected from the beam splitter to the prism 36 avoids air bearing components (not shown) located under the plate. The prism 36 provides a "dog leg" in the beam path that elevates the beam 24b so that it is horizontal and directed onto the reticle face 14b at the aforementioned grazing angle. It should also be noted that because the beam is fanned by the scanner mirror before it enters the splitter 32, both the upper and lower split beams 24a and 24b are scanned laterally across the reticle.

A pair of electro-optical light collecting assemblies 38, 38 are arranged symmetrically about the scanning regions on opposite sides of the reticle 14. Each assembly 38 includes an optical light collecting and relay system, preferably a multiplet of cylindrical lenses 40, which have excellent resolution in the scanning regions and a large numerical aperture. In the preferred form shown, each multiplet 40 is a triplet as shown in detail in FIGS. 4 and 5. Preferably the lens system 40 is capable of resolving narrow fields of view 19, 19 lying in the scanning regions of the faces 14a and 14b. The fields of view 19, 19 each extend laterally over the projection image area on the reticle surface (typically 105 mm) and longitudinally for approximately 0.5 mm. This lens system collects and relays scattered light from a detecting region 19, 19 to a generally rectangular image plane. Fiber optic concentrator assemblies 42 are provided for transmitting the collected light from the image plane to respective photomultiplier tubes 44.

Figure 4:
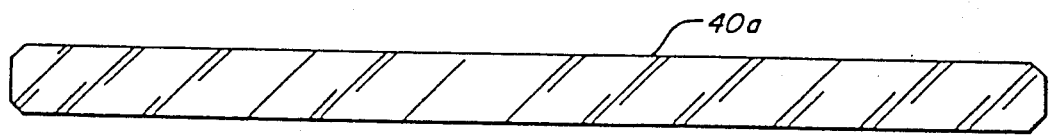
FIG. 4 is a view, in front elevation, of the first element of the triplet of FIG. 3.
Figure 5:
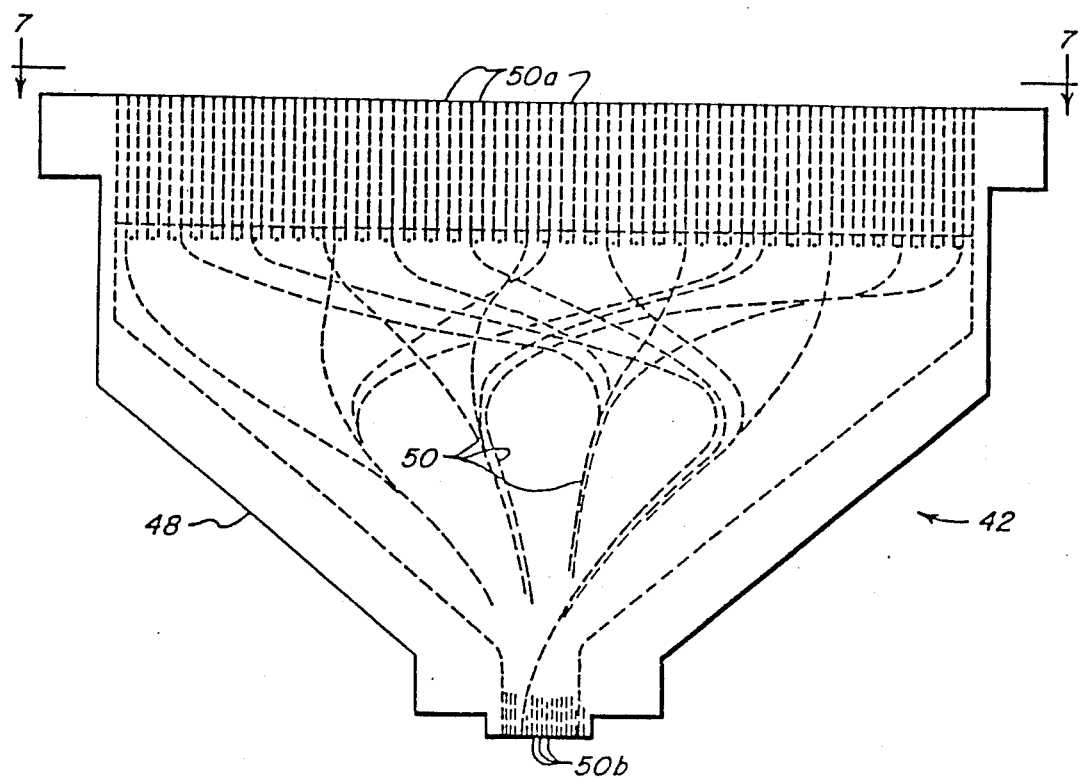
FIG. 5 is a top plan view of a fiber optic light coupling and concentrating assembly employed in the apparatus of FIGS. 1 and 2.
Figure 6:
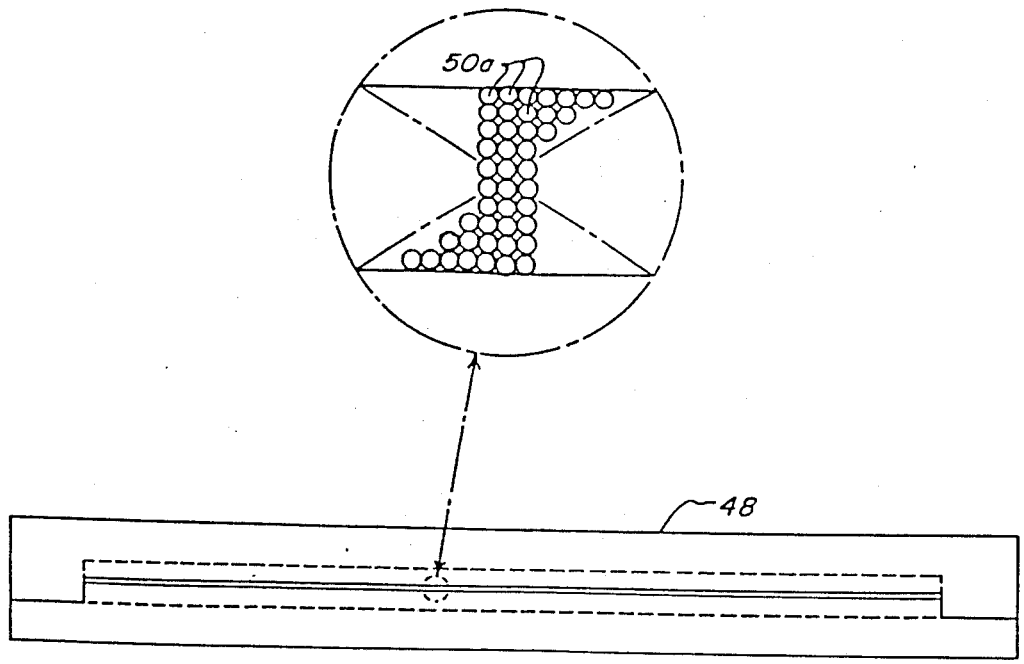
FIG. 6 is a front face view of the fiber optic assembly of FIG. 5.

With reference to FIGS. 4 and 5, each cylindrical lens triplet 40 includes a first lens element 40a, a second lens element 40b, and a third lens element 40c with an aperture stop 46 located between the first and second elements. Each of the lenses 40a, 40b, and 40c, is cylindrical and has a longitudinal axis which preferably extends at least the width of the field of view 19 and preferably extends beyond both the lateral ends of the associated field of view 19 a sufficient distance to subtend a conical half angle of 10 degrees when viewed from a point at the edge of the reticle image area.

By way of illustration but not of limitation, the lens elements 40a, 40b, and 40c are preferably formed of glass having an index of refraction of approximately 2.44. Each lens element has a length, measured along its longitudinal axis, of approximately 135 mm and a height of approximately 10 mm. The first lens 40a is a converging element with a planar first surface and a second surface with the radius of curvature of 8.91 mm. The lens 40b, also converging, is spaced from the element 40a by 1 mm. The lens 40b has a convexly curved first surface with a radius of curvature of approximately 8.91 mm and a planar second surface. The lens 40c is a diverging element having a concave first surface with a radius of curvature of 14.21 m and a planar second surface. The peripheries of the second and third elements are in contact. The first surface of the lens 40a is disposed approximately 13 mm from the field of view 19. Each of the lenses 40a, 40b, and 40c have a maximum thickness measured along the principal optical axis of approximately 3.5 mm. The lens system 40 has an image plane located approximately 9.15 mm beyond the second surface of the lens 40c.

Figure 7:
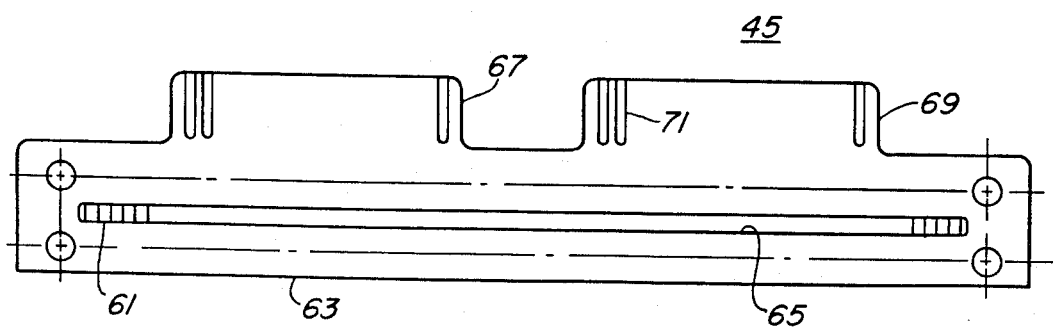
FIG. 7 is a front face view of an electro-optic shutter array which is interposed between the triplet lens of FIGS. 3 and 4 and the fiber optic assembly of FIGS. 5 and 6.

Each fiber optic concentrator assembly 42 includes a generally fan shaped housing 48 which encloses a mass of fine optical fibers 50 each having a first end 50a (as best seen in FIG. 7) lying in the image plane of the cylindrical lens triplet 40 and adapted to receive the scattered light collected by the lens. Each of the fibers 50 are clad to efficiently transmit the light collected at its end 50a to an output end 50b. The fiber ends 50a are generally arrayed along a line extending the length of the cylindrical lens triplet and extending vertically for a sufficient distance to collect and transmit along the fibers 50 substantially all of the light incident upon the associated lens system 40. In the preferred form, the fibers have a diameter of approximately 0.05 mm and are stacked approximately 10 deep at their input ends 50a (see detail in FIG. 7). The fibers are preferably randomly oriented and grouped into four or five bundles before they are secured into a tightly packed, "spot" light emitting configuration which irradiates the cathode of the photomultiplier tube 44. Adjacent fibers ends 50a or 50b are generally parallel and square with respect to the axis of the fiber. The assembly 42 provides an efficient device for a "line to spot" transformation of the light output of the associated lens system 40.

As thus far described, the detection system is essentially the same as that described in previously identified U.S. Letters Pat. No. 4,402,607 whose disclosure is incorporated herein by reference. However, in accordance with the present invention, there is interposed between each of the triplet lenses 40 and its respective fiber optic assembly 42 an electro optic shutter array 45.

As is understood by those skilled in the art, certain ceramic and crystalline materials change their optical properties in the presence of an electrical field and can thus, in conjunction with other optical elements such as polarizers, be utilized as electrically controllable shutters. One such material is lead lanthanum zirconate titanate, usually referred to as PLZT. Arrays of such shutters are available from the Communications Systems Group of Motorola, Inc. located in Albuquerque, New Mexico and also from the Honeywell Ceramics Center, located in New Hope, Minn.

The array 45 employed in the particular embodiment illustrated was fabricated by Honeywell and comprises a linear array of sixty four individually addressable shutter elements, each having an area of about two by two mm. The area of the overall array substantially coincides with the image plane between each cylindrical lens system 40 and the respective fiber optic assembly 42. With reference to FIG. 7, it may be seen that the individual shutter elements, designated by reference character 61, are arranged in a linear array and supported on a substrate 63 having an elongate aperture 65 which coincides with the image space formed by the respective cylindrical lens system 40. Substrate 63 is formed with a pair of integral edge card type connectors 67 and 69 providing appropriate electrical contacts 71 suitable for connection to external drive circuitry. Printed circuit leads (not shown) are provided from one electrode of each shutter element to a respective one of the contacts 71 while the other electrode of each shutter element is connected to a common ground lead.

The function of each shutter array 45 is to block unwanted regular components in the optical signal reaching the respective photo multiplier 44. Such components may conveniently be referred to as "pattern noise". For example, even in the absence of a dust particle or surface flaw, the illuminated area of an optically unpolished surface will scatter back significant light in the direction of the beam source. While a particle or flaw will also scatter light directly back, a greater proportion of the scattered light will be directed off to the sides. Accordingly, by blocking the light which is scattered directly back from the illuminated spot, a relative advantage is given to the desired optical signal components, i.e. the irregular components which are generated by particles or surface flaws. This is, in effect, a form of spatial filtering.

In that the illuminated spot is not stationary but rather is being scanned in order to inspect a large area of surface, the present invention provides a scannable spatial filter, i.e. a spatial filter which is shiftable along the scan line in synchronism with the scanning of the illuminating laser beam. The circuitry for performing this synchronized scanning is illustrated in FIG. 8.

Each of the electro-optical shutter elements is controlled by a respective high voltage driver circuit 102. Each of these driver circuits is in turn controlled by a respective stage in a 64-bit shift register 104. In the embodiment illustrated, the shift register 104 is loaded with a single bit which is then shifted along the register to effect actuation of the successive shutters in sequence. Synchronization of this sequential operation of the shutters with the scanning of the laser beam is accomplished as follows.

As is described in greater detail in the aforementioned U. S. Letters Pat. No. 4,402,607, scanning of the laser beam is effected by an oscillating mirror, the mirror being driven by a suitable waveform, e.g. a sawtooth or triangular wave, so as to obtain a reasonably linear scan with respect to time.

Figure 8:
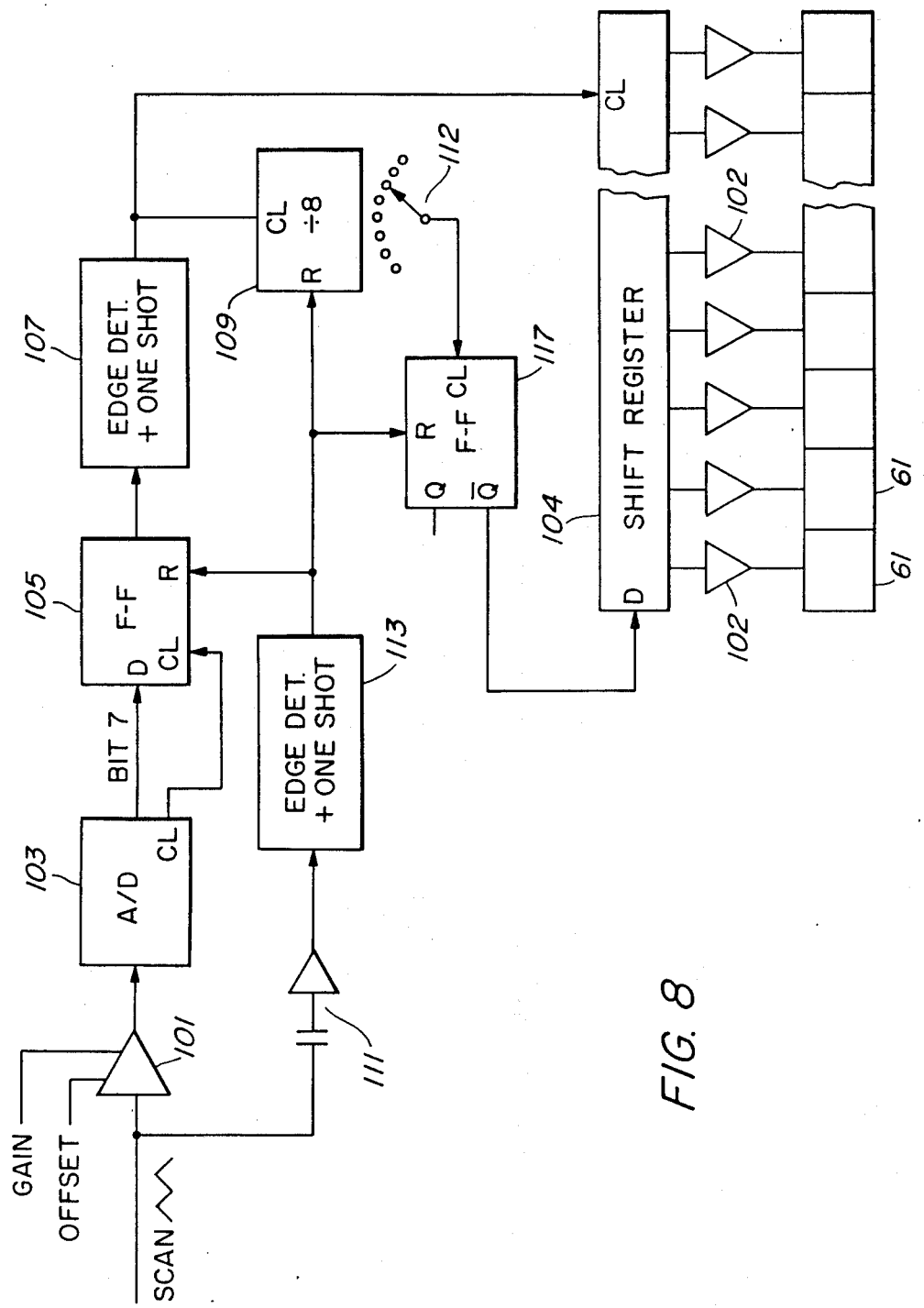
FIG. 8 is a block diagram of the control circuity which operates the electro-optic shutter array of FIG. 7.

With reference to FIG. 8, this scan drive waveform is applied initially to a buffer amplifier 101 which is provided with adjustable gain and offset. These adjustments, in effect, allow the digitization process which controls the shutter array to be, in effect, spatially aligned with the optical scanning. From the buffer amplifier 101, the scanning waveform is applied to an A-to-D converter 103. Converter 103 is operated in a self-clocking mode, i.e. conversions are performed substantially at its free running rate. While the commercially available converter employed provides 8 bits of resolution, only one bit is in fact utilized by the control circuitry of FIG. 8.

The least significant bit provided by the converter 103 is provided to the data input of a d-type flipflop 105 and the clock signal developed by the converter, i.e. the signal which indicates completion of an A-to-D conversion, is applied to the clock input of the d-type flipflop 105 also. It will thus be understood that the output of the d-type flipflop will change state only when the value of BIT 7 of the converted signal changes state from a previous conversion. An edge detector and one-shot circuit 107 provides a positive-going pulse of predetermined duration for each transition in the output value from the d-type flipflop 105 whether positive or negative going. The pulse train generated by the edge detector and one-shot circuit 107 is applied as the clock input to the shift register 104.

In order to determine the proper time to start a shutter scanning sequence, the mirror scanning signal is applied also to a differentiator 111 to develop a squarewave which is essentially synchronized with the sawtooth scanning waveform. An edge detector and one-shot circuit 113 generates a positive-going pulse of predetermined duration for each transition in the output signal of the differentiator 111, whether positive or negative going. The output pulse from the one-shot circuitry 113 is applied to reset the divide-by-eight counter 109, the d-type flipflop 105 and also a set/reset flipflop 117. Flipflop 117 is employed to introduce the single bit which is shifted along the shift register 104 to effect sequential operation of the shutter elements as described previously. The clock input for the flipflop 117 is taken from one of the output lines of the divide by eight counter 109, the selection being made by switch 112.

In that the scanning mirror must typically be allowed to overscan the actual area to be inspected, i.e. to allow for the finite mechanical response of the mirror system, a selectable delay is provided before a bit is introduced into the shift register to initiate the sequence of operation of the shutter elements. This delay is provided by a divide-by-eight counter 109 which is clocked by the same signal as the shift register.

Briefly, the operation of the FIG. 8 circuitry is as follows. When the sawtooth or triangular wave controlling the scanning mirror changes direction, the edge detector and one-shot circuitry 113 resets the flipflops 105 and 117 and also resets the counter 109. As the scan drive waveform progresses in its linear fashion, the A-to-D converter 103 together with the latch 105 and edge detector and one-shot circuitry 107 develop a series of clock pulses, each of which corresponds to a preselectable portion of the total linear scan. However, until a number of such clock pulses have passed, determined by the setting of switch 110, no data bit is entered into the shift register 104 so no operation of the shutters will take place. When the preselected count is reached however, a single bit will be introduced into the shift register and will be propagated along the shift register in synchronism with the linear scan.

Since the clock pulses applied to the shift register are derived from the instantaneous amplitude of the scan waveform rather than from an independent clock, it can be seen that each shutter element will be turned on, i.e. put into a light blocking state, just at the time the beam is illuminating the surface point which is most directly aligned with that shutter element. Accordingly, the unwanted regular component of back scatter will be blocked from the photomultiplier. On the other hand, a lateral scattering from the illuminated area, i.e. as is characteristic of a flaw or particle, will be picked up by light passing through the other shutters which remain open.

While the particular embodiment described by way of illustration herein employs only a single actuated shutter element at any one time, it should be understood that more complex shifting patterns might also be employed. For example, certain types of reticle patterns can develop fairly well-defined side lobes, e.g. at 45 degrees to either side of the main direction of incidence. If desired, a more complex pattern of data may be entered into the shift register to provide a more complex pattern which is shifted in synchronization with the laser beam to block such additional regular components also.

Still further, while a straightforward linear scan has been illustrated together with a linear array of electro-optical shutters, it should be understood that the present invention can be extended to more complex scanning patterns, e.g. raster scans or circular scans, and that, in conjunction with such scans, a two-dimensional array or matrix of electro-optical devices may be used which are energized in a moving pattern corresponding to the unwanted regular optical signal components.

In view of the foregoing, it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. Surface inspection apparatus comprising:
   means for generating a light beam;
   means for scanning said beam in a line across a surface to be inspected;
   photodetector means;
   optical means for collecting light scattered from said surface along said line and coupling the collected light to said photodetector;
   an elongate array of electro-optical shutters adjacent said line and optically interposed between said scanning means and said coupling means;
   means for operating said shutters in a shifting pattern in synchronism with said scanning to block light scattered directly toward said coupling means and thereby improve the detectability of light scattered transversely to said coupling means by an irregularity associated with said surface.

2. Apparatus as set forth in claim 1 wherein said line is essentially straight.

3. Apparatus as set forth in claim 2 wherein said apparatus includes a cylindrical lens system for collecting scattered light and wherein said shutters are arranged in an essentially straight line between said lens and said photodetector means.

4. Apparatus as set forth in claim 3 further comprising a fiber optic assembly for collecting light from a linear field formed by said lens system and concentrating said light in a spot adjacent said photodetector.

5. Apparatus as set forth in claim 1 wherein said shutters are controlled in response to data stored in a shift register and said data is shifted along said shift register to effect the shifting pattern of energization of said shutters.

6. Apparatus as set forth in claim 1 wherein said data comprises a single bit which is shifted along said shift register to operate that shutter which is aligned with the area of the surface then being illuminated by said beam.

7. Apparatus as set forth in claim 6 wherein said scanning means comprises a mirror driven by a triangular waveform and clocking of said shift register is controlled by digitizing the amplitude of said waveform.

8. A surface inspection apparatus comprising:
   means for generating a light beam;
   means for scanning said beam across a surface to be inspected;
   photodetector means;
   optical means for collecting light scattered from said surface and coupling the collected light to said photodetector;
   an array of electro-optical shutters optically interposed between said scanning means and said coupling means; and
   means for operating said shutters in a pattern shifting in synchronism with said scanning to block light scattered directly toward said coupling means and thereby improve the detectability of light scattered transversely to said coupling means by an irregularity associated with said surface.

* * * * *